United States Patent

Mallow

Patent Number: 5,810,595

Date of Patent: Sep. 22, 1998

[54] DENTAL REPAIR COMPOSITION AND METHOD

[75] Inventor: William A. Mallow, Helotes, Tex.

[73] Assignee: Southwest Research Institute, San Antonio, Tex.

[21] Appl. No.: 683,321

[22] Filed: Jul. 18, 1996

[51] Int. Cl.$^6$ ...................................................... A61C 5/00
[52] U.S. Cl. ........................................ 433/228.1; 433/226
[58] Field of Search ............................. 433/217.1, 222.1, 433/226, 228.1

[56] References Cited

U.S. PATENT DOCUMENTS

| | | |
|---|---|---|
| 3,785,832 | 1/1974 | Bowen . |
| 4,051,302 | 9/1977 | Mayama et al. . |
| 4,069,214 | 1/1978 | Onizawa . |
| 4,102,856 | 7/1978 | Lee, Jr. . |
| 4,514,527 | 4/1985 | Bowen . |
| 4,588,756 | 5/1986 | Bowen . |
| 4,659,751 | 4/1987 | Bowen . |
| 4,964,911 | 10/1990 | Ibsen et al. . |
| 5,133,957 | 7/1992 | Suh et al. . |

OTHER PUBLICATIONS

Project No. 7 RO 3 DE10794–02, Kao, Elizabeth C. "Improved Amino Acid–Modified Dental Glass Ionomers", 1994.

Project No. 5 R01 DE10177–03, Marshall, Sally J. "Development of EDTA–Derivative Dentin Bonding Systems". 1994.

Project No. 5 P50 DE09307–07, Soderholm, Karl–Johan M. "Conditioning and Bonding Agents for Resin Based Composites", 1995.

*Primary Examiner*—Nicholas D. Lucchesi
*Attorney, Agent, or Firm*—John L. Sigalos

[57] ABSTRACT

A composition for use in repair of teeth in which a dibasic amino acid partially esterified with allyl alcohol or a hydroxyacrylate or methacrylate and cyclicized, is utilized and the method of tooth repair comprising applying the composition to a tooth requiring repair and curing the composition.

19 Claims, No Drawings

DENTAL REPAIR COMPOSITION AND METHOD

The instant invention relates to a composition suitable for dental repair; i.e., a dental filling or dental adhesive, and to the method of its use for such purposes.

There have been repeated efforts to replace amalgam as a filling in dental practice, as well as to have suitable adhesives for dental purposes other than for fillings. One polymeric material that has been suggested for such use is bis-glycidylmethylmethacrylate polymer (bis-GMA). When used as a dental adhesive or filling, together with the other usual components admixed therewith, such bis-GMA offers good mechanical and physical properties, but exhibits considerable post-shrinkage and relatively poor adhesion to bone substrate. Thus, it is not entirely satisfactory for use as an adhesive in dental work or as a filling. The use of such GMA material is disclosed in U.S. Pat. Nos. 4,588,756 and 4,964,911.

U.S. Pat. No. 4,659,751 discusses the use of a variety of acids and other materials in order to treat the surface of teeth, such as enamel and dentin, to activate the surfaces for improved adhesion to polymers, but no disclosure or suggestion is made therein of the use of the GMA or bis-GMA.

In this regard, it is well known that in order to achieve desired bonding on enamel or dentin, the protein coatings on the enamel and the smear level on dentin must be removed. Traditionally, this has been done utilizing organic acids such as phosphoric, citric, and lactic acids, as well as ethylene diamine dicarboxylic acid. Accordingly, many of the new products provide such polyacids as surface cleaning and priming agents for enamel and dentin. At the present time bis-GMA resins themselves are not inherently adhesive to tooth surfaces, and if used acid etching is required.

SUMMARY OF THE INVENTION

The present invention overcomes the problems of the prior art and provides dental compositions with and without bis-glycidylacrylates which have excellent mechanical properties and resistance to shrinking, and have good adhesion to the dentin enamel and do not require any acid etching to teeth prior to being applied.

Briefly stated, the present invention comprises a composition for use in repair of teeth comprising a dibasic amino acid partially esterified with allyl alcohol or a hydroxyalkyl acrylate or methacrylate and cyclicized.

The invention further comprises such compositions including a bis-glycidylacrylate polymer.

The instant invention also comprises the method of tooth repair utilizing such compositions as hereinafter described, in which UV activation is used to form the final hardened polymer.

DETAILED DESCRIPTION

As to the hydroxyl acrylate or methacrylate used, it is preferred to use 2-hydroxyethyl methacrylate (HEMA), although any hydroxy $C_1$ to $C_4$ allyl acrylate or methacrylate can be used. Examples are 2-hydroxyethyl acrylate (HEA), 2-hydroxypropyl acrylate (HPA), hydroxypropyl methacrylate (HPMA), allyl alcohol and the like. The invention will be described in connection with HEMA.

As used herein the term "bis-GAA" refers to bis-glycidylalkylacrylate polymers in which the alkylacrylate is a $C_1$ to $C_{12}$ acrylate or methacrylate Particularly useful are bis-glycidylmethylmethacrylate, bis-glycidylethylmethacrylate, bis-glycidylmethylacrylate, bis-ethylacrylate and mixtures thereof.

As to the dibasic amino acids used in the esterification, those utilized are glutamic and aspartic acids. The gamma-carboxyl group of these basic amino acids is very reactive to primary alcohols and relatively reactive to secondary alcohols.

In accordance with the present invention, a controlled esterification is carried out in order to produce the partial esters that are desired. The object is to prepare a monoester; i.e., to esterify only one of the carboxy groups and have available for further reaction amino and carboxyl functional groups. It is recognized that minor amounts of diesters may be formed.

The partial esterification of the existing hydroxyl groups on the HEMA is implemented utilizing any conventional esterification procedure with a variety of solvents and solvent blends to assure solubility and reactivity. Examples are dioxane, acetonitrile, tetahydrofuran (THF) and crown ethers.

In carrying out the reaction the HEMA is combined with less than stoichiometric amounts of dibasic acid. It is preferred to use 10 to 50% of the stoichiometric amount of glutamic or aspartic acid in the presence of mineral acids such as of sulfuric or hydrochloric acid, organosulfonic acids such as thionyl chloride, paratoluenesulfonic acid, or acid salts. Some disesterification may occur, but it is minimal and can be avoided by slowly adding HEMA to the amino acid and heating to temperatures of about 40° to 50° C. to produce the partial ester of the amino acid. This requires about 30 to 90 minutes and the optimum time is dependent primarily on the particular reactants, proportions thereof, and reaction temperatures and is readily determined by routine experimentation.

The resultant partial ester, usually a half ester of the dibasic acid, is then separated from the solvent by any of the known processing methods such as conventional solvent/non-solvent, precipitation/crystallization. A suitable example is use of acetone/$H_2O$ at 4:1 followed by cooling to −20° C., filtering off crystals produced, and a crystallization in acetone/$H_2O$.

After the partial ester is prepared the amino groups are cyclicized into N-carboxyl anhydrides (NCA). Such cyclization is well-known and phosgene is conventionally used to effect the cyclization.

The relevant cyclicized partial ester is preferably combined with the bis-GMA and the usual fillers and reinforcing agents approved for use to produce a composition suitable for use as a dental filling and which will be resistant to abrasion and oral environmental attack. Examples are Bioglass, tantalum oxide nanoclusters, and the like which can also contribute to X-ray opacity. It will be understood that the composition can be used for adhesive purposes.

As to proportions of bis-GAA and cyclicized HEMA partial ester of amino acids used to form the dental repair composition, it is preferred to use 1 part by weight of the cyclicized HEMA ester for each 1 to 10 parts by weight of the bis-GAA. The proportions of the other components are discussed below.

To form the dental composition for use, the bis-GAA and cyclicized HEMA ester, with the other components are admixed just prior to use, applied to the tooth or teeth, and polymerized. As the bis-GAA and cyclicized HEMA ester react to cross-link, the NCA component of the HEMA ester is opened and $CO_2$ released. This released $CO_2$ acts to form microbubbles in the mass as it cures, which microbubbles by their expansive action counteract any shrinkage of the mass. Thus, the acrylic copolymerization and NCA reaction are coordinated so the $CO_2$ released can be effective in preventing shrinkage.

The copolymerization is preferably a light activated one, suitably by UV activation in which conventionally known peroxide curing agents, such as cumene hydroperoxide are utilized.

In use the dentist or dental technician simply admixes the acrylic reactants and other components, the mixture placed in the tooth, and ultra-violet light used to activate and effect the polymerization (cure). In short, a UV activated, peroxide initiated, addition polymerization is effected.

It is believed that since there are still carboxyl groups present that there will be no need for any of the traditional acidic cleaning of enamel or dentin as is presently done prior to using the instant composition. It is believed that the amino groups also present will aid in adhesion, even if no acidic cleaning is utilized.

As to the fillers added to the composition there can be used reinforcing fillers such as Bioglass (a calcium-phosphate silicate) and fillers such as silica, corundum, tantalum oxide, and tantalum oxide nanoclusters, or mixtures of the foregoing. For each 100% by volume of the bis-GMA/HEMA partial ester mixture there can be added from about 50 to 85% by volume of such fillers.

Optimally, to help prevent cracks in any filling over time, milled fibers such as quartz fibers, corundum fibers, or silicon nitride fibers can be incorporated as part of the composition in an amount of about 0.1 to 2% by volume for each 100% by volume of the bis-GMA/HEMA partial ester.

To help plasticize the mixture, it is also desirable to add neat HEMA which acts to prevent the mixture from becoming too viscous. Other acrylates and methacrylates, such as hydroxyethylacrylate, isopropylidene bis [2,(3)-hydroxy-3 (2)-(4phenoxy) propyl methacrylate, decamethyl dimethacrylate, ethylhexyl acrylate-bis GMA comonomer. Mixtures thereof, and the like approved for human use can also be used. They are added in amounts required to assure flow of the composition into tooth crevices to provide most suitable fillings, the amount used can be as low as 1 to 2%, based on the total weight of the composition with the optimum amount for any given composition being determined by routine experimentation.

It will be understood that in addition to dental usage, the instant composition can also be used as a bone cement.

The invention will be further described in connection with the following examples which are set forth for purposes of illustration only.

EXAMPLE 1

2 moles of HEMA were added dropwise to a 0.5 mol slurry of 1-aspartic acid in dioxane at ~50° C. The aspartic acid slurry contained ~50 ml of concentrated $H_2SO_4$.

The mixture was stirred and maintained at ~50°–60° C. for about 2 hours to permit completion of the reaction. Completion was determined by noting that the aspartic acid solids had dissolved.

The partial ester was recovered by solvent/non-solvent precipitation/crystallization using acetone/$H_2O$ (4:1), cooling to −20° C., filtering and recovering the crystals, and redissolving the crystals on acetone/$H_2O$ (4:1) and re-cooling to form the purified ester crystals.

EXAMPLE 2

The process of Example 1 is followed except that 0.5 mol of 1-glutamic acid is substituted for the 1-aspartic acid. An equally suitable partial ester is obtained.

EXAMPLES 3 AND 4

The processes of Examples 1 and 2 are followed except that 2.0 moles of HEEA (hydroxethyl ethacrylate) is substituted in each Example for the HEMA. In each case suitable partial esters are obtained.

EXAMPLE 5

The partial ester of Example 1 is phosgenated to cyclicize the amino acid groups into N-carboxyl anhydrides, using a conventional phosgenation process.

Namely, the partial ester is first purged with $N_2$ and then with phosgene at room temperature. The solution is then heated at 40°–60° C. and purged with $N_2$ to remove HCl.

EXAMPLE 6

Bis-GMA, a highly viscous material is mixed with a low viscosity acrylic plasticizer, HEMA, to form a first mixture.

Separately, the cyclized HEMA ester of Example 5 is admixed with tantalum oxide nanoclusters to form a second mixture.

At time of use, the two mixtures in the ratio of 1 part by weight of the second mixture to 4 parts by weight of the first mixture and cumene hydroperoxide added thereto.

The composition is placed in the tooth and exposed to ultra-violet light and cured to form a rigid mass.

EXAMPLE 7

The processes of Examples 3 and 4 are followed except that allyl alcohol is substituted for the HEMA used therein. In each case more stable partial esters are obtained which are also capable of co-polymerization with bis-GMA.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A composition for use in repair of teeth, comprising a cyclicized partial ester of a dibasic amino acid with allyl alcohol or a hydroxylacrylate or methacrylate.

2. The composition of claim 1 wherein said cyclicized partial ester is a monoester.

3. The composition of claim 2 including, for each party by weight of said cyclicized partial ester, from 1 to 10 parts by weight of a bis-glycidylalkylacrylate.

4. The composition of claim 3 including a plasticizer.

5. The composition of claim 4 wherein the plasticizer is 2-hydroxyethyl methacrylate.

6. The composition of claim 1 wherein the dibasic amino acid is esterified with allyl alcohol.

7. The method of tooth repair comprising applying the composition of claim 1 to an area of the tooth requiring repair and curing said composition.

8. The method of claim 7 wherein the cyclicized partial ester is a monoester.

9. A composition for use in repair of teeth, comprising a cyclicized monoester of a dibasic amino acid with allyl alcohol or a hydroxyacrylate or methacrylate and, for each part by weight of said cyclicized monoester, from about 1 to 10 parts by weight of a bis-glycidylalkylacrylate.

10. The composition of claim 9 including a plasticizer.

11. The composition of claim 10 wherein the plasticizer is 2-hydroxyethyl methacrylate.

12. The composition of claim 9 wherein the disbasic amino acid is esterified with allyl alcohol.

13. The composition of claim 12 including, for each part by weight if said cyclicized monoester, from 1 to 10 parts by weight of a bis-glycidylakylacrylate.

14. The composition of claim 13 including a plasticizer.

15. The composition of claim 14 wherein the plasticizer is 2-hydroxyethyl methacrylate.

16. The method of tooth repair comprising applying the composition of claim 9 to an area of the tooth requiring repair and curing said composition.

17. The method of claim 16 wherein said composition includes a plasticizer.

18. The method of claim 17 wherein the plasticizer is 2-hydroxyethyl methacrylate.

19. The method of claim 18 wherein a peroxide initiator is included in the composition and the composition is cured by UV activation.

* * * * *